United States Patent
Fujimoto et al.

(10) Patent No.: US 7,252,643 B2
(45) Date of Patent: Aug. 7, 2007

(54) GUIDE WIRE

(75) Inventors: Katsuharu Fujimoto, Kobe (JP);
Hideo Satou, Fujinomiya (JP);
Shunichi Uchino, Fujinomiya (JP)

(73) Assignee: Terumo Kabushiki Kaisha,
Shibuya-Ku, Tokyo (JP)

( * ) Notice: Subject to any disclaimer, the term of this patent is extended or adjusted under 35 U.S.C. 154(b) by 316 days.

(21) Appl. No.: 10/352,101

(22) Filed: Jan. 28, 2003

(65) Prior Publication Data
US 2003/0181828 A1   Sep. 25, 2003

(30) Foreign Application Priority Data
Jan. 28, 2002   (JP)   ............... 2002-019165

(51) Int. Cl.
*A61B 5/00*   (2006.01)
*A61M 25/00*   (2006.01)

(52) U.S. Cl. .................................. 600/585
(58) Field of Classification Search ............... 600/585; 604/164.13; 420/1
See application file for complete search history.

(56) References Cited

U.S. PATENT DOCUMENTS

| | | | |
|---|---|---|---|
| 4,538,622 A | | 9/1985 | Samson et al. |
| 4,748,986 A | * | 6/1988 | Morrison et al. ............ 600/585 |
| 4,953,553 A | * | 9/1990 | Tremulis ..................... 600/486 |
| 5,120,308 A | * | 6/1992 | Hess ....................... 604/170.01 |
| 5,174,302 A | * | 12/1992 | Palmer ......................... 600/585 |
| 5,195,954 A | * | 3/1993 | Schnepp-Pesch et al. ...... 604/22 |
| 5,341,818 A | | 8/1994 | Abrams et al. |
| 5,345,945 A | | 9/1994 | Hodgson et al. |
| 5,606,981 A | * | 3/1997 | Tartacower et al. .......... 600/585 |
| 5,706,826 A | * | 1/1998 | Schwager .................... 600/585 |
| 5,865,768 A | * | 2/1999 | Orr .............................. 600/585 |
| 5,876,356 A | * | 3/1999 | Viera et al. .................. 600/585 |
| 5,957,903 A | | 9/1999 | Mirzaee et al. |
| 5,980,471 A | * | 11/1999 | Jafari .......................... 600/585 |
| 6,280,539 B1 | | 8/2001 | Abrams et al. |
| 6,287,292 B1 | * | 9/2001 | Fariabi ........................ 604/531 |
| 6,491,648 B1 | * | 12/2002 | Cornish et al. .............. 600/585 |
| 6,687,548 B2 | * | 2/2004 | Goode ......................... 607/119 |
| 6,716,183 B2 | * | 4/2004 | Clayman et al. ............ 600/585 |

FOREIGN PATENT DOCUMENTS

WO    WO 97/44084 A2   11/1997

\* cited by examiner

*Primary Examiner*—Max Hindenburg
*Assistant Examiner*—Jonathan Foreman
(74) *Attorney, Agent, or Firm*—Buchanan Ingersoll & Rooney PC (57) ABSTRACT

A guide wire includes a wire body, a first coil, a second coil, and an elongate member. The first coil has a helical shape, and is disposed on a distal end side of the guide wire. The second coil has a helical shape, and is disposed on a distal end side of the first coil. The elongate member has a section that extends a longitudinal direction of the wire body. At least a portion of the section is located inside the second coil, and the elongate member is formed integrally with the first coil or the second coil.

21 Claims, 11 Drawing Sheets

GUIDE WIRE

BACKGROUND OF THE INVENTION

1. Field of the Invention

The present invention relates to a guide wire used for introducing a catheter into a body cavity such as a blood vessel.

2. Description of the Related Art

For example, in case when a catheter is introduced into a blood vessel in the vicinity of the heart, such as the coronary artery, a guide wire is inserted through the catheter and the distal end of the guide wire goes ahead of the catheter while a desired path is properly selected whenever the guide wire meets a diverging point of blood vessels as branching off like a labyrinth.

Such a guide wire was disclosed by the gazette of U.S. Pat. No. 4,538,622. The guide wire is equipped with a wire body, which is a cylindrically shaped element, a first metal coil, a second coil, and a rounded structure. The first coil is fixed to the distal end of the wire body. The second coil is fixed to the distal end of the first coil. The rounded structure is fixed to the second coil. The jointed part of the first and the second coils is fixed to the wire body, which is inserted through the coils, by means of a soldering or brazing material. The brazing material and the rounded structure is bridged by a safety ribbon (refer to FIG. 2 and others of the above gazette).

It is found that a doctor who uses such a guide wire often bends the distal end of the guide wire in a certain desired shape in order to match the shape of the distal end of the catheter with the shapes of blood vessels or in order to guide it more smoothly around the branching points of blood vessels. Bending the distal end of the guide wire in a desired shape is called shape giving, or reshaping.

In case of the guide wire of the aforementioned U.S. Pat. No. 4,538,622, the safety ribbon is a separate component independent from the first coil and the second coil. Therefore, it presents a shortcoming that the fixed end of the safety ribbon may come loose when the safety ribbon is under a tensile strength during the reshaping process. When there is a concern for the safety ribbon to come off, the distal end of the guide wire cannot be formed into a desired shape and a sufficient reshaping effect may not be achieved.

When the wire body is made of Ni—Ti alloy for the benefit of super elasticity, the reshaping process is particularly difficult. Thus, it is necessary to provide a safety ribbon made of a material that can be reshaped easily such as stainless steel separate from the wire body.

Moreover, if the wire body is made of a Ni—Ti alloy, the wettability of soldering is poor, thus resulting in poor joint strength. Therefore, although the safety ribbon is provided, the fixation of the wire body and the coil or others can come loose, so that the safety ribbon, which is provided independently, can also come loose due to the force applied during the reshaping process.

In order to increase the joint strength of soldering, it is necessary to use a special procedure of covering the area with a preliminary tin while shutting out the contact with air after removing the oxide layer on the metal surface of the Ni—Ti alloy. This requires additional time and labors in the manufacturing process.

Those are the reasons why the selection ranges of the materials for the wire body and the safety ribbon are substantially narrowed. This makes it difficult to achieve the objective of reshaping, especially, in maintaining an appropriate flexibility in the distal end of the guide wire.

SUMMARY OF THE INVENTION

It is therefore a general object of the invention to provide a guide wire that makes the reshaping of the distal. end thereof more easily and securely.

More specifically, it is an object of the invention to provide a guide wire including a wire body, a first coil, a second coil, and an elongate member. The first coil has a helical shape, and is disposed on a distal end side of the guide wire. The second coil has a helical shape, and is disposed on a distal end side of the first coil. The elongate member has a section that extends a longitudinal direction of the wire body. At least a portion of the section is located inside the second coil, and the elongate member is formed integrally with the first coil or the second coil. This makes it possible to achieve the reshaping of the distal end of the guide wire more easily and securely.

It is another specific object of the invention to provide a guide wire including a wire body, a helical coil, and an elongate member. The helical coil has a distal end and a proximal end and is disposed on a distal end side of the wire body. The elongate member extends from the distal end or the proximal end of the coil, is disposed inside the coil, formed integrally with the coil, and made of a material that can be reshaped.

It is a further specific object of the invention to provide a guide wire including a distal end side wire, a proximal side wire, a helical coil, and an elongate member. The distal end side wire is made of Ni—Ti alloy. The proximal side wire is made of a material with rigidity higher than that of said distal end side wire. The helical coil has a distal end and a proximal end, is disposed on the distal end sidewire, and is radiopaque at least at the distal end thereof. The elongate member can be reshaped, is made of the same material as the coil, and extends into inside of the coil from either the distal end or the proximal end of the coil.

The objects, features, and characteristics of this invention other than those set forth above will become apparent from the description given herein below with reference to preferred embodiments illustrated in the accompanying drawings.

BRIEF DESCRIPTION OF THE DRAWING

FIG. 6A through FIG. 6E are perspective views of first through fifth modifications of an elongate member respectively.

DETAILED DESCRIPTION OF THE PREFERRED EMBODIMENT

The embodiments of this invention will be described below with reference to the accompanying drawings. For the sake of convenience of description, let us call the right side of FIG. 1 through FIG. 3, FIG. 6A through FIG. 6E, and FIG. 7 through FIG. 11 as "the proximal end direction," and the left side thereof as "the distal end direction."

Figure 1:
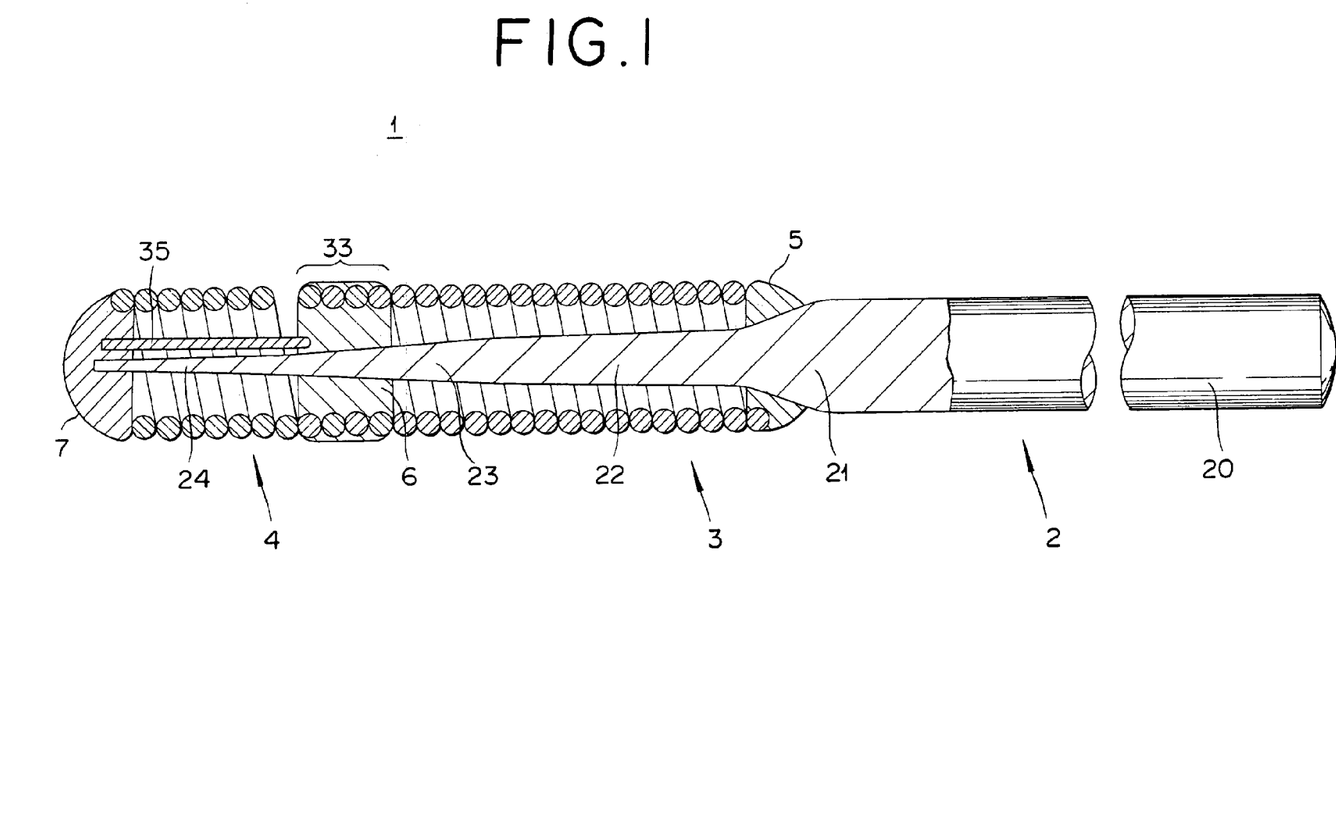
FIG. 1 is a vertical section of a guide wire according to a first embodiment of the invention.

A guide wire 1 shown in FIG. 1 is used as inserted into a catheter that is introduced into a body cavity such as a blood vessel. The guide wire 1 includes a wire body 2, which is a core wire, a first coil 3 having a helical shape, a second coil 4 having a helical shape, and at least one elongate member 35. The wire body 2 is a main part of a guide wire 1. The first coil 3 is located on the distal end side of the wire body 2. The second coil 4 is located on the distal end side of the first coil 3 and is jointed there. The elongate member 35 has a section that extends in the lengthwise direction of the wire body 2. Moreover, a part of the extending portion is located inside the second coil 4.

The wire body 2 is preferably made of a metallic material and consists of a body section 20, a first taper section 21, an intermediate section 22, a second taper section 23, and a small diameter section 24 as shown in FIG. 1. The body section 20 has a relatively large diameter. The first taper section 21 and the second taper section 23 are both located toward the distal end direction away from the body section 20. The outer diameters of the first taper section 21 and the second taper section 23 reduce gradually toward the distal end direction. The intermediate section 22 is located between the first taper section 21 and the second taper section 23. The outer diameter of the intermediate section 22 is substantially constant in the longitudinal direction. The small diameter section 24 is located toward the distal end direction away from the second taper section 23.

A portion of the wire body 2 located on the distal end side relative to the first taper section 21 is inserted substantially in center of the inside of the first coil 3 or the second coil 4. In the arrangement shown in the drawing, the portion of the wire body 2 is inserted inside the first coil 3 and the second coil 4 without contacting them. A portion of the proximal side of the first coil 3 may be contacting the wire body 2. The metal that forms the wire body 2 can be stainless steel or a super elasticity alloy such as Ni—Ti base alloy.

Since the guide wire 1 has the first taper section 21 and the second taper section 23, the rigidity of the wire body 2 can be reduced gradually toward the distal end direction. Therefore, it is possible to increase its maneuverability in the insertion process without causing any bending problems.

The wire body 2 can be formed by using a single material such as stainless steel or Ni—Ti alloy, or a combination of different materials. "Ni—Ti alloy" may have a third element, such as copper (Cu), aluminum (Al), iron (Fe), zinc (Zn) or cobalt (Co) may be used. For example, it is possible to form the body section 20, which is located on the proximal side, with a material of a relatively high rigidity such as stainless steel, and form the sections located on the distal end side away from the body section 20, i.e., the first taper section 21, the intermediate section 22, the second taper section 23, and the small diameter section 24 of the first embodiment with a material of a smaller rigidity than stainless steel, for example, Ni—Ti alloy.

In this case, the guide wire 1 can have excellent insertion characteristic and torque transmissibility, thus providing an excellent maneuverability. Moreover, the distal end side of the guide wire 1 provides excellent flexibility and recovery capability, resulting in an improved blood vessel following capability and safety.

The combination of different materials in the wire body 2 is not limited to the above example but can be arbitrarily selected depending on the purpose. For example, when at least one of the intermediate section 22, the second taper section 23, and the small diameter section 24 is made of stainless steel, it is possible to improve the shape preserving capability in the reshaping process.

It is also possible to form the body section 20 and the sections away from the body section 20 toward the distal end direction with the same material, such as Ni—Ti alloy, but with different rigidity characteristics, thus causing the body section 20 and the sections away from the body section 20 toward the distal end direction to have different rigidity characteristics. Specifically, it can be so arranged that the body section 20 to have a higher rigidity due to the difference in materials compared to the sections away from the body section 20 toward the distal end direction.

The first coil 3 is preferably made of a metallic material. The helical part of the first coil 3 should be densely formed so that no gaps exist in a state when no external force is applied. The metallic material that forms the first coil 3 can be stainless steel, super elastic alloy such as Ni—Ti alloy, shape memory alloy, or cobalt base alloy. The first coil 3 can also be made of a radiopaque material, which is described later.

The proximal section of the first coil 3 is fixed to the first taper section 21 of the wire body 2. The fixing method is not limited in particular. In the first embodiment, a fixing material 5 such as soldering or brazing material is used as shown in FIG. 1. Other fixing methods are, for example, welding or bonding with an adhesive material.

The second coil 4 is preferably made of a metallic material. The helical part of the second coil 4 should be densely formed so that no gaps exist in a state when no external force is applied. The metallic material that forms the second coil 4 can be stainless steel, super elastic alloy such as Ni—Ti alloy, shape memory alloy, cobalt base alloy, a precious metal, or an alloy containing the precious metal. The precious metal can be gold, platinum, and tungsten.

It is preferable to make the second coil 4 from a radiopaque material, such as a precious metal. By doing so, it is possible to insert the guide wire 1 into a living body while monitoring the position of the distal end of the guide wire 1 under the X-ray radioscopy as the guide wire 1 generates an X-ray image.

If the first coil 3 is made of a super elastic alloy, the elongate member 35 that extends from the distal end of the first coil 3 is to be made of the same alloy. In this case, the elongate member 35 is required to be heat treated or cold formed for the reshaping capability.

If the second coil 4 is made of a radiopaque material such as stainless steel, it is possible to form a layer made of a radiopaque material as mentioned above on at least a part of either one of the surfaces of the second coil 4, the elongate member 35 to be described later, and the small diameter section 24. Since the guide wire 1 generates an X-ray image in this case as well, it is possible to insert the guide wire 1 into a living body while monitoring the position of the distal end of the guide wire under the X-ray radioscopy.

Figure 2:
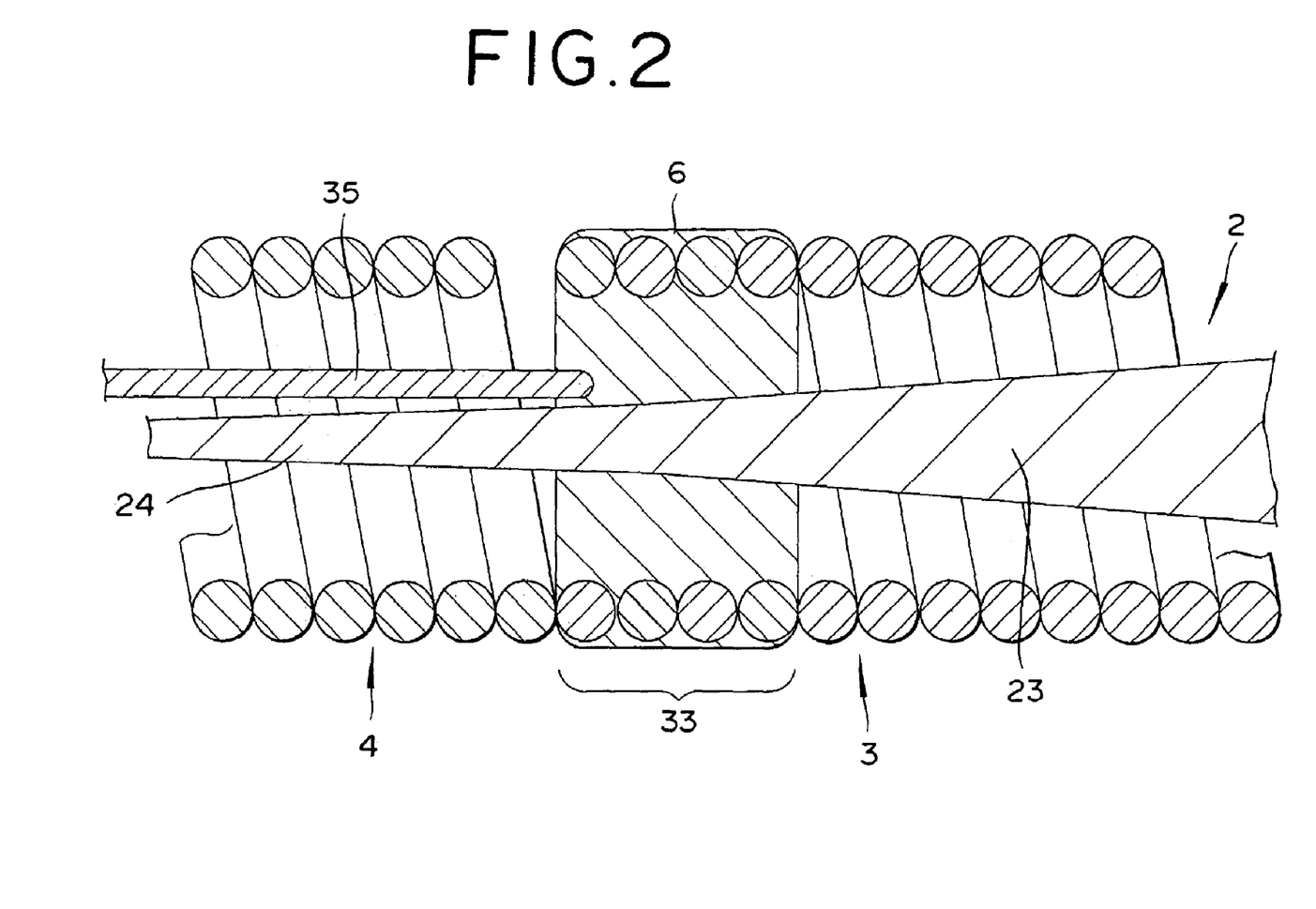
FIG. 2 is an enlarged vertical section of a joint area between a first coil and a second coil in the guide wire shown in FIG. 1.

The proximal end of the second coil 4 is connected and fixed to the distal end of the first coil 3. The disposing and fixing methods for the first coil 3 and the second coil 4 are not limited in particular. In the first embodiment, it is so disposed that a portion of the first coil 3 overlaps a portion of the second coil 4. Specifically, as shown in FIG. 2, the helical windings of the first coil 3 and the second coil 4 are intermeshing with each other in a joint section 33 where the first coil 3 and the second coil 4 are connected. In other words, the helical windings of the first coil 3 and the second coil 4 are intermeshed together in such a way that each winding of them appears between the windings of the other coil.

By arranging that way, the first coil 3 and the second coil 4 can be disposed accurately concentric with each other as they are being assembled. When a force is applied in such away as to pull the guide wire toward the distal end direction, such an arrangement effectively prevent its separation from the joint section 33.

The joint section 33 is fixed to the second taper section 23 of the wire body 2. The fixing method is not limited in particular. In the first embodiment, a fixing material 6 such as soldering or brazing material, is used as shown in FIG. 1 and FIG. 2. This makes the strength of connection of the first coil 3 and the second coil 4 to the wire body 2 stronger. Other fixing methods can be welding and bonding with adhesive.

Although wires with circular cross sections are used for the first coil 3 and the second coil 4 in the first embodiment, the invention is not limited by them. Wires with elliptical, rectangular, in particular, of oblong cross sections can be used as well.

The material, diameter or thickness, and cross-sectional shape of wires used for the first coil 3 and the second coil 4, as well as the helical pitch, outer diameter, inner diameter, etc., of the first coil 3 and the second coil 4 can be equal or different.

The surfaces of the first coil 3 and/or the second coil 4, in particular, the entire or a portion of the outer surface thereof, should preferably be coated with a hydrophilic or hydrophobic material (not shown). This makes the insertion of the guide wire 1 smoother.

Such a coating can be made in various configurations depending on the purpose. For example, modifications 1 through 3 described below are some of them. In the modification 1, a lubricating hydrophobic coating is applied on the entire outer surfaces of the first coil 3 and the second coil 4. In the modification 2, a lubricating hydrophobic coating is applied on a portion of the second coil 4 for a predetermined length on the distal end of the second coil 4, while a hydrophilic coating is formed on the first coil 3 and other part of the second coil 4. In the modification 3, no coating is applied on a portion of the second coil 4 for a predetermined length on the distal end of the second coil 4, while a hydrophilic or hydrophobic coating is formed on the first coil 3 and other part of the second coil 4.

The hydrophilic material for forming the coating can be cellulose polymeric materials, polyethylene oxide polymeric materials, maleic anhydride polymeric materials, acrylamide polymeric materials, water soluble Nylon, and polyvinyl alcohol. The maleic anhydride polymeric materials here can be, for example, maleic anhydride copolymers such as methylvinylether-anhydride copolymer. The acrylamide polymeric materials here can be block copolymers of polyglycidyl methacrylate-dimethyl acrylamide (PGMA-DMAA). The hydrophobic material for forming the coating can be fluorocarbon resins such as polytetrafluoroethylene and silicone materials. The coating can be formed on the surface of the wire 2 as well.

As shown in FIG. 1 through FIG. 4, the elongate member 35 is disposed on the distal end of the first coil 3. The elongate member 35 is formed to extend from the distal end of the first coil 3, while extending substantially parallel to the small diameter section 24 inside the second coil 4.

The existence of the elongate member 35 makes it possible to easily and securely execute the aforementioned reshaping process. For example, if a doctor is reshaping the distal end of the guide wire 1 using the fingers, the elongate member 35 makes a plastic deformation to produce a desired shape and serves the purpose of maintaining the desired shape.

The materials of the elongate member 35 and the first coil 3 are the same, and the elongate member 35 is formed integrally with the first coil 3. That is, the elongate member 35 and the first coil 3 are a single unitary part. Therefore, it requires a fewer parts compared to a case of forming the elongate member 35 as a separate part, thus enabling it to assemble, i.e., produce the guide wire 1 easily.

Figure 4:
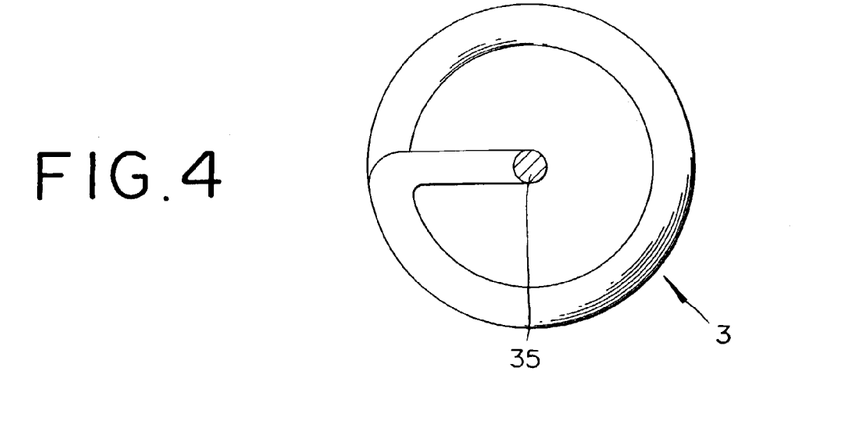
FIG. 4 is a front view taken on line IV-IV of FIG. 3.

As shown in FIG. 4, the elongate member 35 is disposed on the center axis or the vicinity of the center axis of the cylinder of the first coil 3. The elongate member 35 can be formed, for example, during the process of forming the first coil 3 from a wire material, i.e., the coiling process.

The length of the elongate member 35 is not limited in particular, but it is preferable to be 0.5 to 4.0 cm, and is more preferable to be 1.5 to 3.0 cm.

The cross sectional area of the entire or a portion of the elongate member 35 should preferably be smaller than the cross sectional area of the wire that forms the first coil 3 or the second coil 4. Specifically, if the cross-sectional shape of the wire material used to form the elongate member 35 and the first coil 3 happens to be circular, the outer diameter of the elongate member 35 is preferably smaller than the outer diameter of the wire material that forms the first coil 3 as shown in FIG. 4. By using such a configuration, a better flexibility can be secured.

Figure 5:
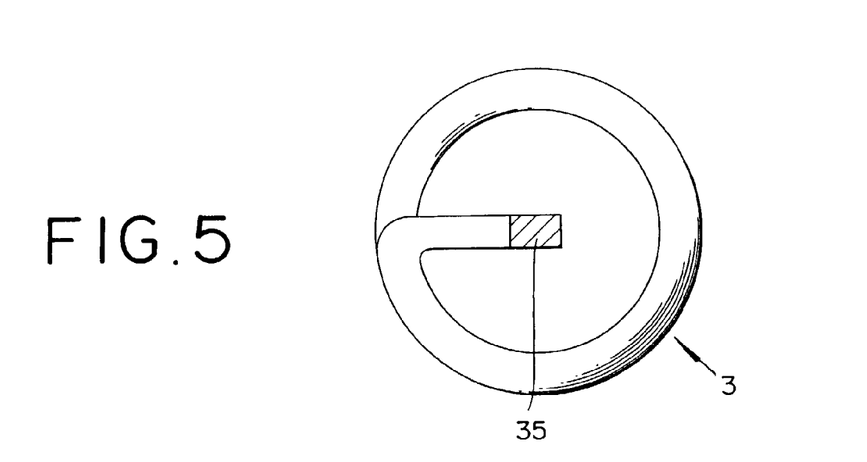
FIG. 5 is a plan view of assistance in explaining a modification of the first coil.

More over, as shown in FIG. 5, the cross-sectional shape of the elongate member 35 can be quadrangular such as square, rectangular, and trapezoidal. For example, the elongate member 35 can be a flat plate or a rectangular rod. In case of an elongate member 35 having a rectangular cross section as shown in FIG. 5, it is easier to bend it in the direction of the long side of the rectangle, i.e., the vertical direction in FIG. 5, than in the transverse direction.

Therefore, it provides an advantage of making it easier to determine the reshape directionality, and also provides a higher flexibility in the direction of the longer side and improves the following deformation capability when the stress is applied. Such a flat plate-like or rectangular rod-like portion can be formed only in certain part of the elongate member 35.

Figure 3:
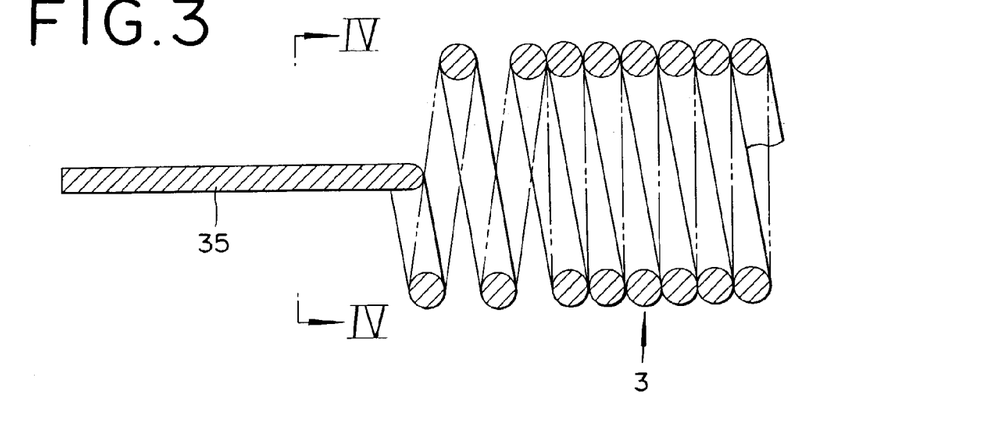
FIG. 3 is a vertical section of assistance in explaining the configuration of the first coil.

The cross-sectional shape of the elongate member 35 can be constant over the entire length. The elongate member 35 can have a portion where the cross-sectional shape changes continuously, i.e., increase or decrease continuously. The shape that is applicable to the elongate member 35 with a circular cross section as shown in FIG. 3 and FIG. 4, can be a shape wherein the outer diameter is constant over the entire length, a shape wherein the outer diameter is gradually decreasing toward the distal end direction, a shape wherein the outer diameter is constant partially, and a shape that has a portion wherein the outer diameter is gradually decreasing toward the distal end direction. In particular, it is preferable that the elongate member 35 has a portion whose cross section area reduces or reduces gradually toward the distal end direction.

Next, modifications 1 through 5 of the elongate member 35 will be described below with reference to FIG. 6A through FIG. 6E. The elongate member 35 according to the modification 1 shown in FIG. 6A has a rectangular cross section shape. The length of the longer side $L_1$ of the rectangle is substantially constant along the longitudinal direction of the elongate member 35. The length of the shorter side $L_2$ of the rectangle reduces gradually toward the direction of the distal end 36 of the elongate member 35. Thus, the length $L_2$ of the shorter side of the rectangle reduces gradually or in steps.

Figure 6A:
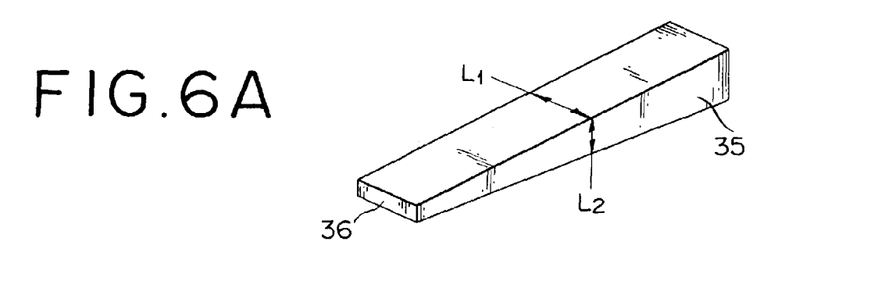
Figure 6B:
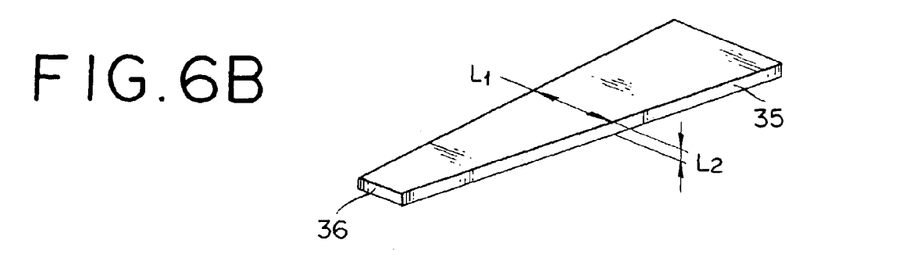

The elongate member 35 according to the modification 2 shown in FIG. 6B has a rectangular cross section shape. The length of the shorter side $L_2$ of the rectangle is substantially constant along the lengthwise direction of the elongate member 35. The length of the longer side $L_1$ of the rectangle reduces gradually toward the direction of the distal end 36. In other words, the length $L_1$ of the longer side reduces gradually or in steps.

Figure 6C:
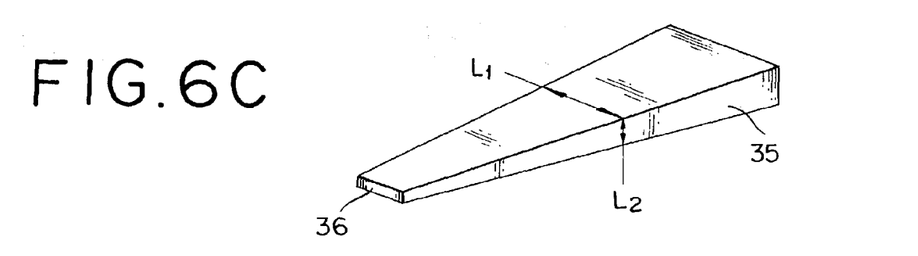

The elongate member 35 according to the modification 3 shown in FIG. 6C has a rectangular cross section shape. The length of the longer side $L_1$ of the rectangle reduces gradually toward the direction of the distal end 36. The length of the shorter side $L_2$ of the rectangle reduces gradually toward the direction of the distal end 36. Thus, both the length $L_1$ of the longer side and the length $L_2$ of the shorter side reduce gradually or in steps.

Figure 6D:
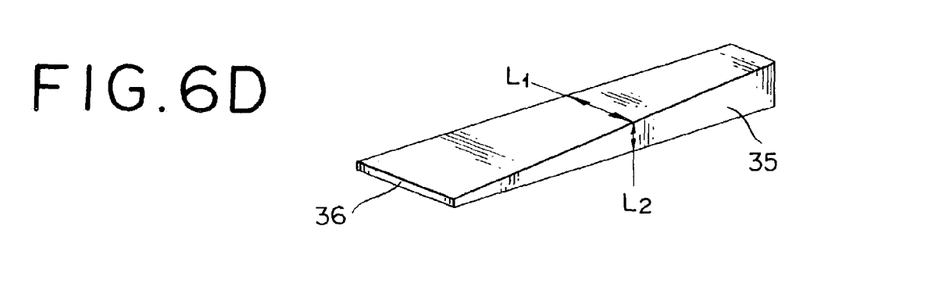

The elongate member 35 according to the modification 4 shown in FIG. 6D has a rectangular cross section shape. The length of the longer side $L_1$ of the rectangle increases gradually toward the direction of the distal end 36. In other words, the length of the longer side $L_1$ of the rectangle increases gradually or in steps. The length of the shorter side $L_2$ of the rectangle decreases gradually toward the direction of the distal end of the elongate member 35. In other words, the length of the shorter side $L_2$ of the rectangle reduces gradually or in steps. In this modification, the cross-sectional area of the elongate member 35 represented as a product of the length of the longer side $L_1$ multiplied by the length of the shorter side $L_2$, can be substantially constant along the lengthwise direction of the elongate member 35.

Figure 6E:
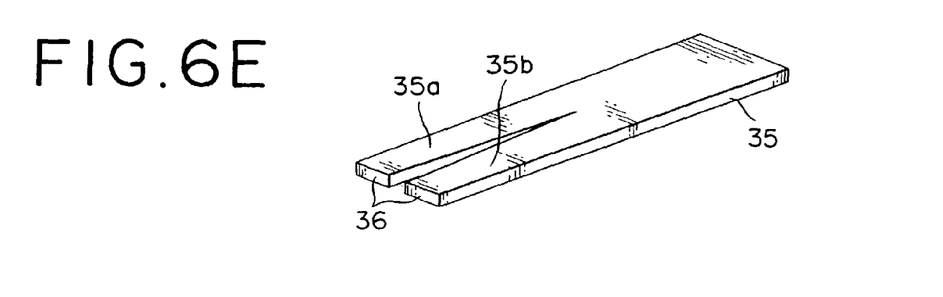

The elongate member 35 according to the modification 5 shown in FIG. 6E is divided into several branches in the middle of the lengthwise direction of the elongate member 35. Specifically, the elongate member 35 has two branches 35a and 35b in the arrangement shown in the drawing. The cross-sectional areas of the branches 35a and 35b should preferably reduce toward the direction of the distal end 36.

The elongate member 35 formed as such increases its flexibility toward the distal end. Therefore, when the distal end of the guide wire 1 gets into contact with the blood vessel, the distal end of the guide wire 1 can bend very easily and smoothly so that any possible damage to the blood vessel may be prevented, thus improving the safety substantially.

A coating of the aforementioned radiopaque material can be disposed on at least a portion of the surface of the elongate member 35. It will provide the X-ray imaging capability to the guide wire 1 regardless of materials of the second coil 4 and the small diameter section 24. Thus, it is possible to insert the guide wire 1 into a living body while monitoring the position of the distal end of the guide wire 1 under the X-ray radioscopy.

As shown in FIG. 1, the distal end of the elongate member 35 and the distal end of the second coil 4 are fixed to the distal end of the wire body 2. The fixing method is not limited in particular. In the first embodiment, a fixing material 7 such as soldering or brazing material, is used. This makes it possible to further increase the jointing strength between the first coil 3 and the second coil 4 and the wire body 2. Other fixing methods are, for example, welding or bonding with an adhesive material. In order to prevent possible damages to the internal wall of the blood vessel, the end face of the fixing material 7 should preferably be rounded.

FIG. 7 through FIG. 11 show vertical sections of the guide wires according to the second through sixth embodiments. In describing the second through sixth embodiments based on these drawings, the descriptions of items that are identical to the corresponding items of the guide wire 1 of the first embodiment shown in FIG. 1 will not be repeated, and the descriptions will mainly be concentrated on the differences.

Figure 7:
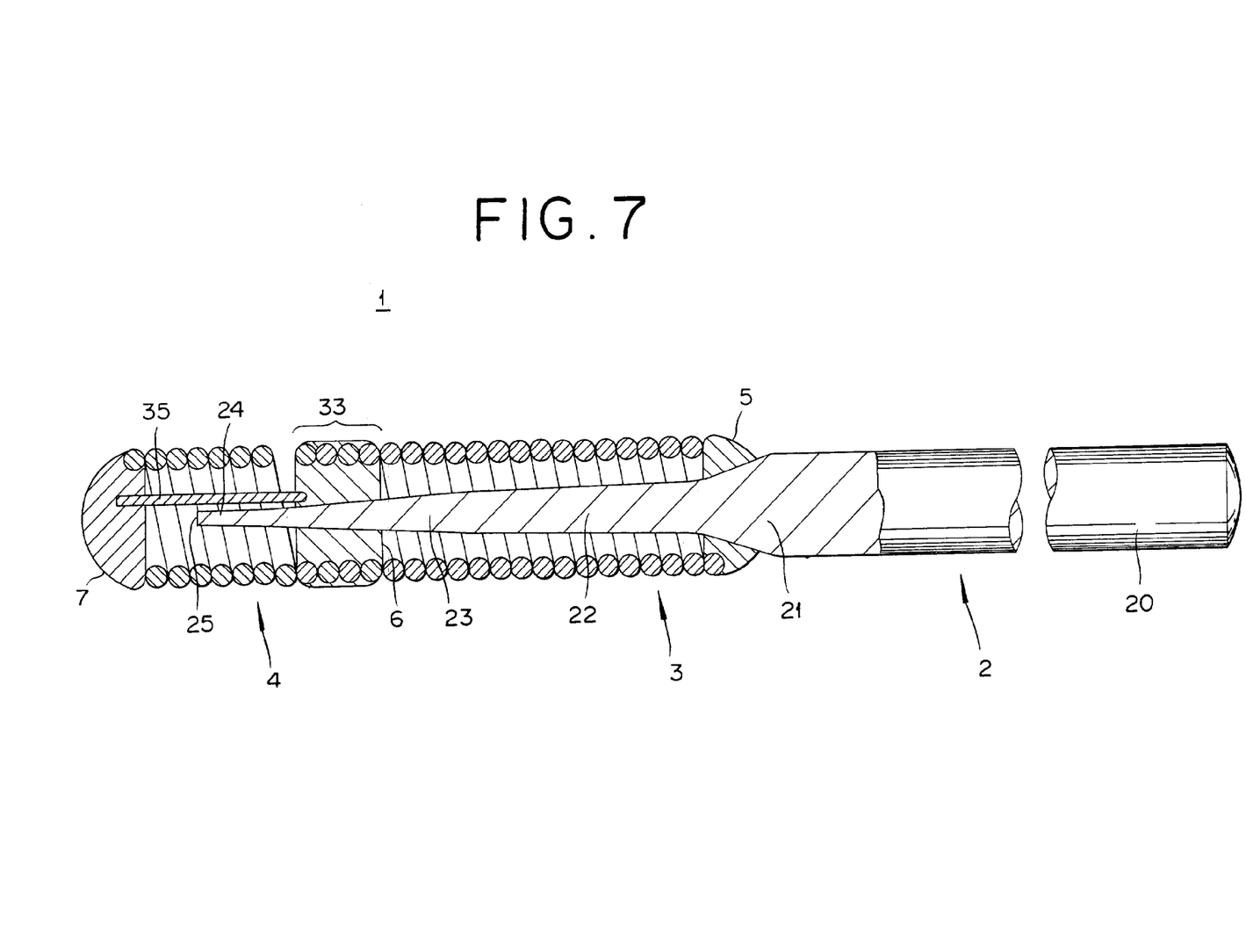
FIG. 7 is a vertical section of a guide wire of a second embodiment of the invention.

The guide wire 1 according to the second embodiment shown in FIG. 7 is different from the first embodiment only in the configuration of the distal end of the wire body 2. Specifically, the small diameter section 24 of the wire body 2 is adapted to be shorter and the distal end 25 of the small diameter section 24 is not fixed by the fixing material 7 but free. Since the distal end 25 of the small diameter section 24 is formed as a free end, the flexibility of the guide wire 1 is further improved.

Moreover, both ends of the elongate member 35 are fixed by the fixing materials 6 and 7 respectively, and the distal end 25 of the small diameter section 24 does not reach the fixing material 7. Consequently, the elongate member 35 serves the function of a "safety wire" for preventing the fall out of the second coil 4 in addition to the function of a reshaping member. For that reason, it can maintain a tensile strength even though the distal end 25 is a free end.

Figure 8:
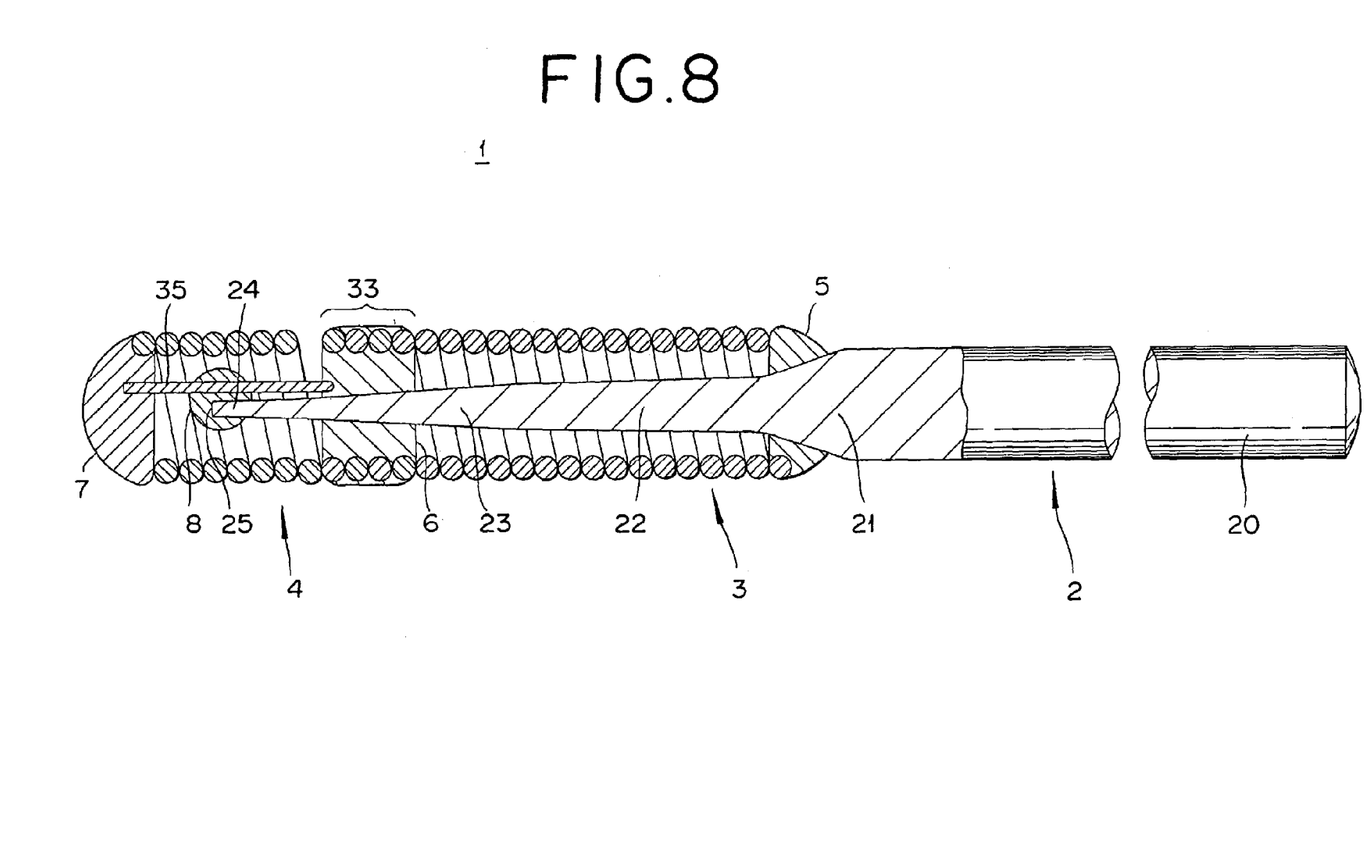
FIG. 8 is a vertical section of a guide wire of a third embodiment of the invention.

The guide wire 1 according to the third embodiment shown in FIG. 8 is different from the first embodiment only in the configuration of the distal end of the wire body 2. Specifically, the small diameter section 24 of the wire body 2 is adapted to be shorter and the distal end 25 of the small diameter section 24 is disposed and fixed in the middle of the elongate member 35. The fixing method is not limited in particular. In the third embodiment, a fixing material 8 such as soldering or brazing material, is used. Other fixing methods are, for example, welding or bonding with an adhesive material.

Since the small diameter section 24 of the wire body 2 is fixed to the elongate member 35, the small diameter section 24 can follow the elongate member 35 easily when the distal end of the guide wire 1 is bent or curved. This improves the capability to follow blood vessels that run and/or branch in a complex manner and prevents the distal end 25 from exposing on the outside of the coil via the gaps formed between the wires as the second coil 4 elongates.

Moreover, both ends of the elongate member 35 are fixed by the fixing materials 6 and 7 respectively, and the distal end 25 of the small diameter section 24 does not reach the fixing material 7. Consequently, the elongate member 35 serves the function of a "safety wire" for preventing the fall out of the second coil 4 in addition to the function of a reshaping member. Therefore, it can maintain a tensile strength even though the distal end 25 is a free end.

Figure 9:
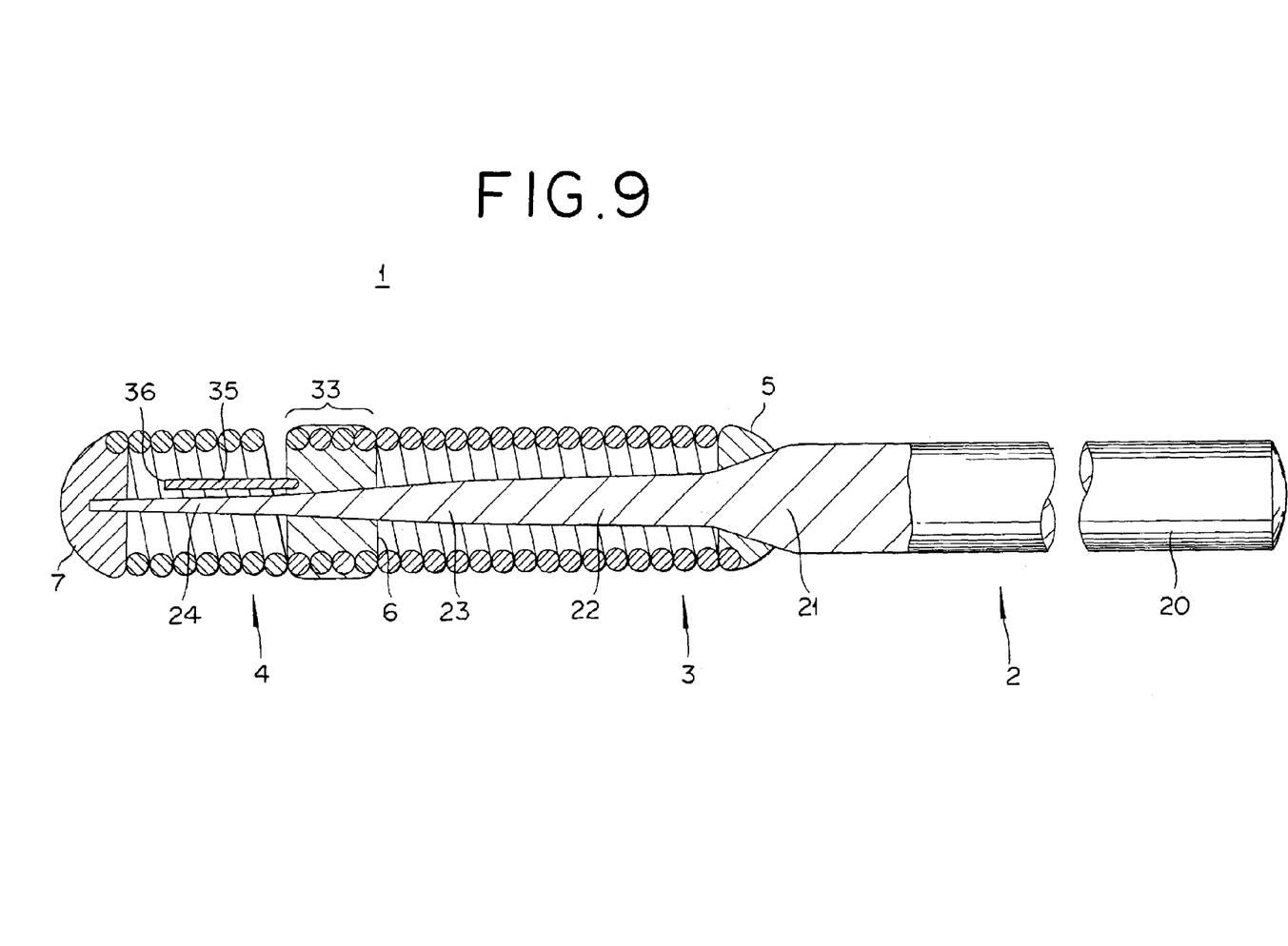
FIG. 9 is a vertical section of a guide wire of a fourth embodiment of the invention.

The guide wire 1 according to the fourth embodiment shown in FIG. 9 is different from the first embodiment only in the position of the distal end 36 of the elongate member 35. Specifically, the elongate member 35 is adapted to be shorter and the distal end 36 of the elongate member 35 is not fixed by the fixing material 7 but is free. Since the distal end 36 of the elongate member 35 is formed as a free end, the flexibility of the guide wire 1 is further improved.

Figure 10:
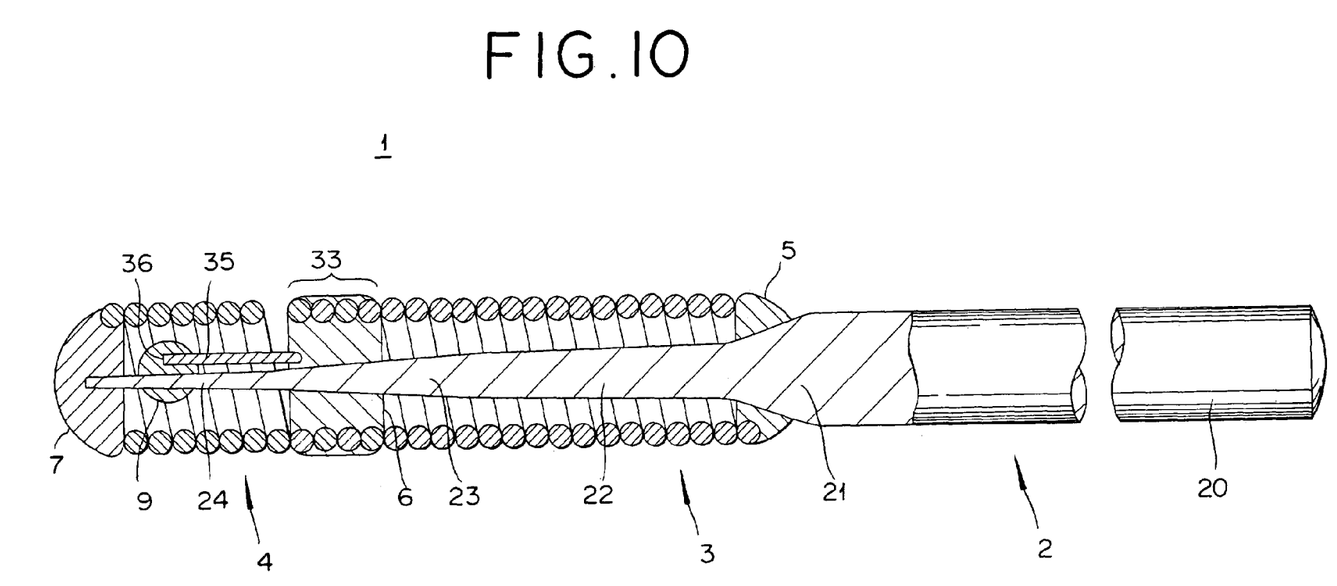
FIG. 10 is a vertical section of a guide wire of a fifth embodiment of the invention.

The guide wire 1 according to the fifth embodiment shown in FIG. 10 is different from the first embodiment only in the position of the distal end 36 of the elongate member 35. Specifically, the elongate member 35 is adapted to be shorter and the distal end 36 of the elongate member 35 is disposed and fixed in the middle of the small diameter section 24. The fixing method is not limited in particular. In the fifth embodiment, a fixing material 9 such as soldering or brazing material, is used. Other fixing methods are, for example, welding or bonding with an adhesive material.

Since the distal end 36 of the elongate member 35 is fixed to the small diameter section 24, the elongate member 35 can follow the small diameter section 24 easily when the distal end of the guide wire 1 is bent or curved. This improves the capability to follow blood vessels that run and/or branch in a complex manner and prevents the distal end 25 from exposing on the outside of the coil via the gaps formed between the wires as the second coil 4 elongates.

Figure 11:
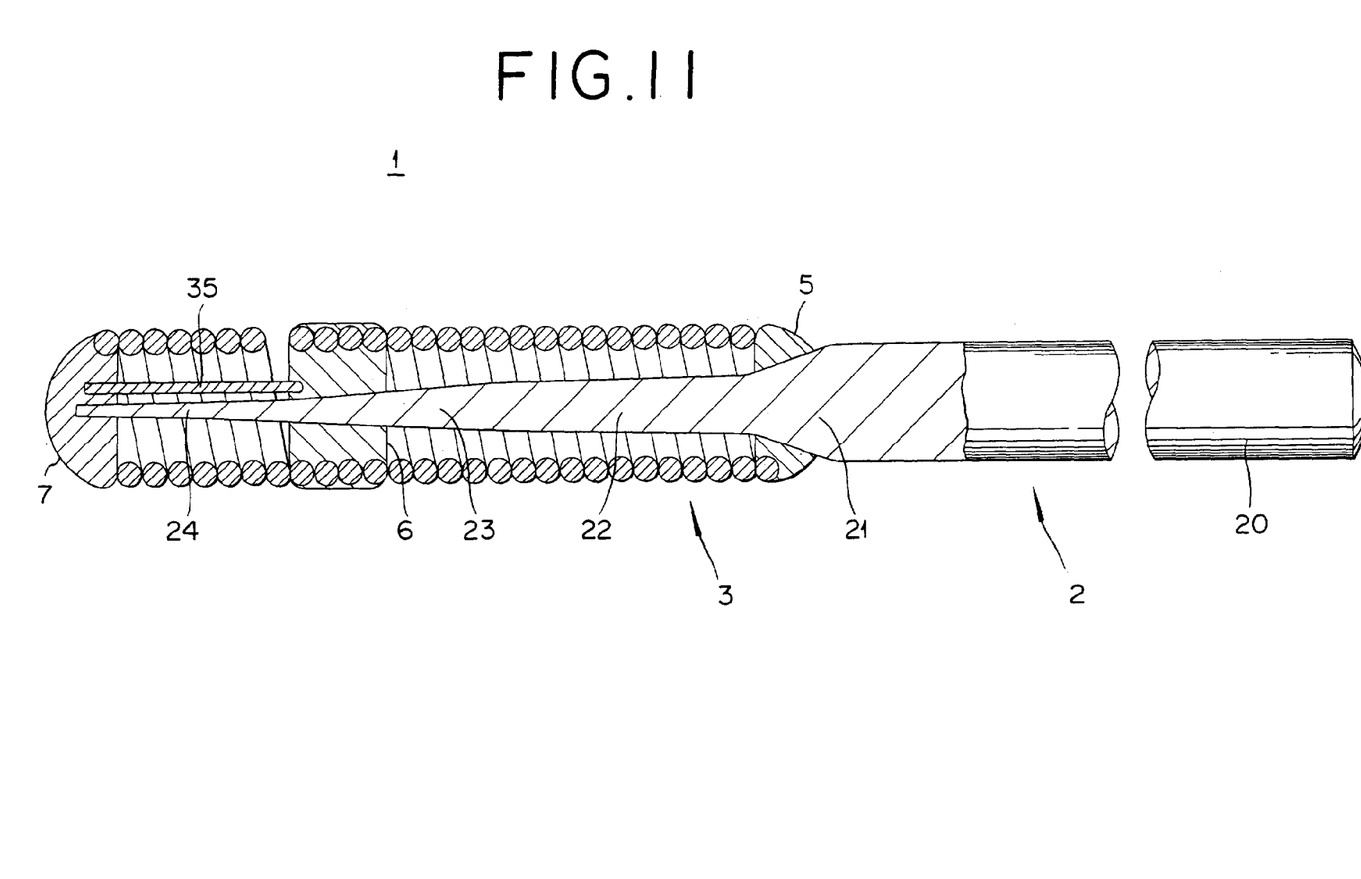
FIG. 11 is a vertical section of a guide wire of a sixth embodiment of the invention.

The guide wire 1 according to the sixth embodiment shown in FIG. 11 is different from the first embodiment in the coil structure of the guide wire. While the coil consists of two coils, i.e., the first coil 3 and the second coil 4, the coil structure of the sixth embodiment consists of a single coil, or the coil 3 alone. The elongate member 35 is disposed in the internal space of the distal end of the coil 3. The elongate member 35 is made from the same material as that of the coil 3 as an integral part and extends into the inside of the coil 3 after making a U-turn at the distal end of the coil 3.

Figure 12:
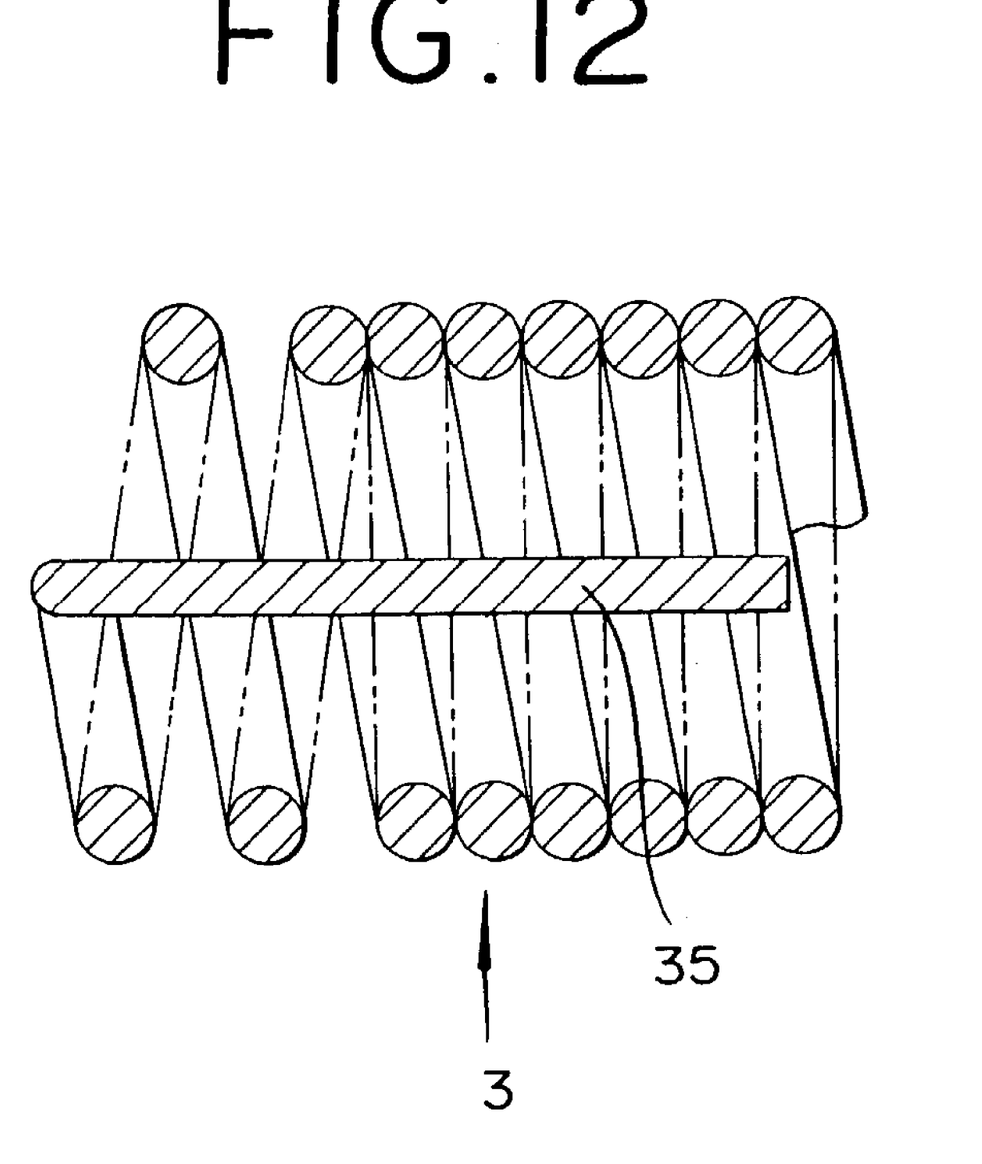
FIG. 12 is a vertical section of assistance in explaining the coil structure of the sixth embodiment of the invention.

FIG. 12 illustrates a state of the elongate member 35 extending from the distal end of the coil 3 as its integral part. As can be seen from the drawing, the elongate member 35 is located substantially in the center of the coil 3. The transitional part from the coil 3 to the elongate member 35 resides inside the fixing material 7 and the proximal end of the elongate member 35 is fixed by being embedded inside the fixing material 6. The material forming the coil 3 and the elongate member 35 is radiopaque and can be reshaped.

In the sixth embodiment, the elongate member 35 extends as an integral part from the distal end of the coil 3, but it can also be formed to extend as an integral part from the proximal end of the coil 3.

As can be seen form the first through sixth embodiments described above, it is possible to widely arrange the flexibility and the bending characteristic of the distal end of the guide wire 1 by properly choosing the combination of the selection of the fixing methods and fixing positions according to the elongate member 35, the second coil 4, and the wire body 2, as well as the selection of the materials, shapes and dimensions according to the composing members such as the wire body 2, the first coil 3, the elongate member 35, and the second coil 4.

Moreover, although the elongate member 35 is formed on the distal end of the first coil 3 as an integral part, the following modifications 1 through 6 can be applied as well.

In modification 1, the elongate member 35 is formed integrally on the proximal end of the first coil 3, extends from the proximal end of the first coil 3 toward the distal end direction, and is inserted into the first coil 3 and the second coil 4, which is connected to the first coil 3.

In modification 2, the elongate member 35 is formed integrally on the proximal end of the second coil 4, extends from the proximal end of the second coil 4 toward the distal end direction, and is inserted into the second coil 4. The elongate member 35 and the second coil are thus a single unitary part.

In modification 3, the elongate member 35 is formed integrally on the distal end of the second coil 4, extends from the distal end of the second coil 4 toward the proximal end direction, and is inserted into the second coil 4 or into both the second coil and the first coil 3.

Modification 4 has two elongate members 35. The first elongate member 35 is formed integrally on the proximal end of the first coil 3, extends from the proximal end of the first coil 3 toward the distal end direction, and is inserted into the inside of the first coil 3. The second elongate member 35 is formed on the proximal end of the second coil 4 integrally, extends from the proximal end of the second coil 4 toward the distal end direction, and is inserted into the inside of the second coil 4. Each elongate member 35 and the respective coil are thus a single unitary part.

Figure 13:
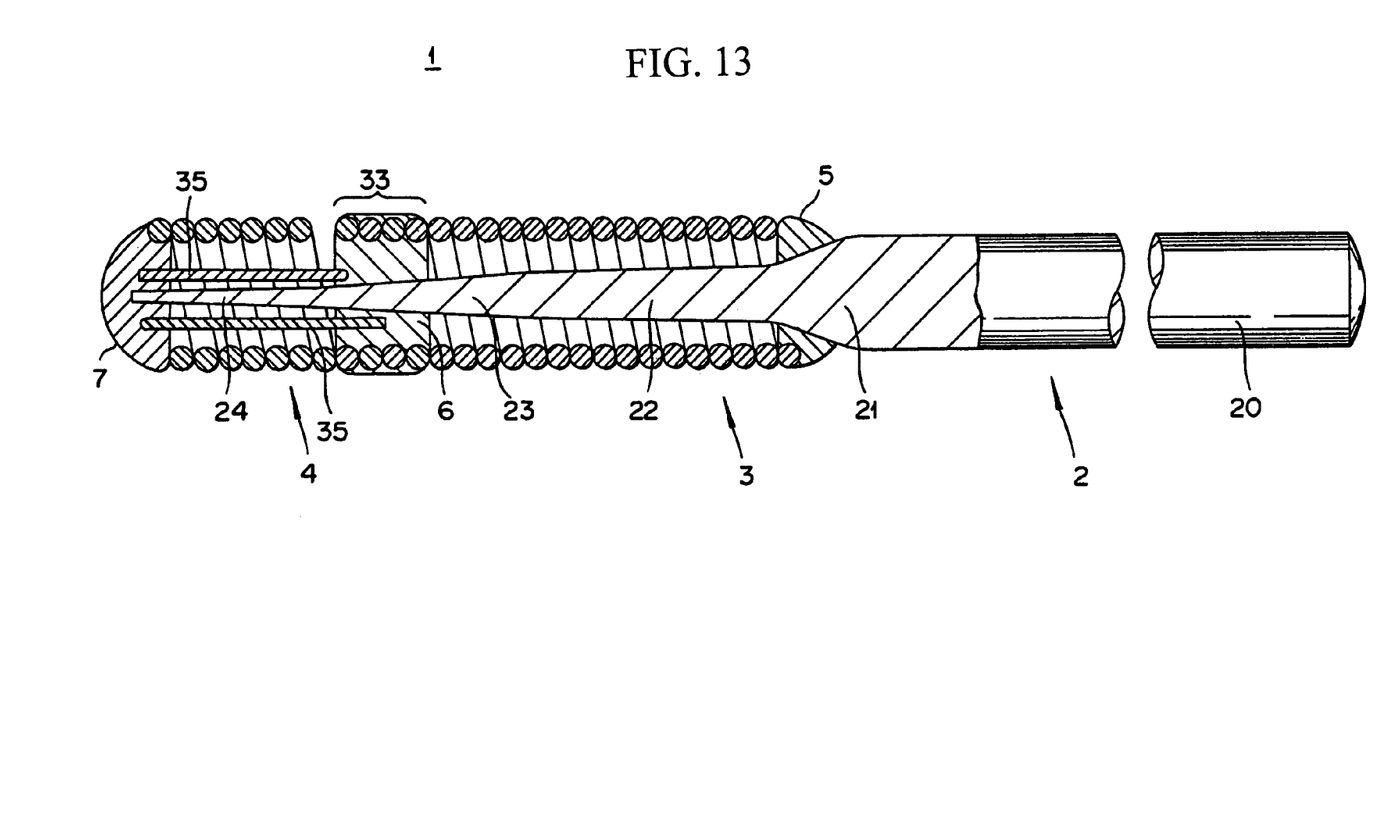
FIG. 13 is a vertical section of a guide wire according to another embodiment illustrating two elongate members.

Modification 5 has two elongate members 35. FIG. 13 generally illustrates a guide wire with this modification. The first elongate member 35 is formed integrally on the distal end of the first coil 3, extends from the distal end of the first coil 3 toward the distal end direction, and is inserted into the inside of the second coil 4. The second elongate member 35 is formed on the proximal end of the second coil 4 integrally, extends from the proximal end of the second coil 4 toward the proximal end direction, and is inserted into the inside of the first coil 3. In this case, the proximal end of the second elongate member 35 can be disposed in any place along the longitudinal direction either at the first taper section 21, the intermediate section 22, or the second taper section 23.

Modification 6 has two elongate members 35. The first elongate member 35 is formed integrally on the distal end of the first coil 3, extends from the distal end of the first coil 3 toward the distal end direction, and is inserted into the inside of the second coil 4. The second elongate member 35 is formed on the distal end of the second coil 4 integrally, extends from the distal end of the second coil 4 toward the proximal end direction, and is inserted into the inside of the second coil 4, or the inside of both the second coil 4 and the first coil 3.

The location of the distal or proximal end of the elongate member 35 in the abovementioned modifications 1 through 6 is not limited in particular. For example, it is possible to fix the distal end of the elongate member 35 at the fixing material 6 or the fixing material 7, or to form a free end for the distal end of the elongate member 35 by disposing it in the middle of the wire body 2, in particular, the small diameter section 24, or to fix the distal end of the elongate member 35 in the middle of the wire body 2, in particular, the small diameter section 24.

As mentioned above, the guide wire according to this invention has an elongate member, which is useful for reshaping the distal end of the guide wire. Therefore, even if the wire body is made of a material that is difficult to give shape thereto, for example, super elasticity alloy, it is possible to secure a sufficient reshape capability at the distal end of the guide wire.

Since the elongate member is formed integrally with the first coil or the second coil, it prevents the elongate member from falling off during reshaping or when using the guide wire. Moreover, it makes it easier to assemble, i.e., manufacture, the guide wire in comparison with a case of forming the elongate member with other material because it uses a lesser number of components.

The guide wire in accordance with this invention is capable of providing an excellent flexibility to the distal end of the guide wire in addition to the abovementioned excellent reshape capability. This is extremely important as it improves the maneuverability and safety during its insertion into a living body.

Moreover, it is possible to widely arrange the flexibility and the bending characteristic of the distal end of the guide wire by properly selecting various conditions such as the materials, shapes, dimensions, fixing method, and fixing areas according to the wire body, the first coil, the second coil and the elongate member.

Thus, the guide wire according to this invention is quite useful when it is applied to a catheter to be inserted into a body cavity such as a blood vessel, as it makes it possible to provide an optimum treatment corresponding to each medical case.

It is obvious that this invention is not limited to the particular embodiments shown and described above but may be variously changed and modified without departing from the technical concept of this invention. In particular, conditions such as the shapes, constructions and locations of the distal end of the wire body, the first coil, the second coil and the elongate member are not limited to the specific examples shown in the embodiments, but rather can be chosen widely as long as they can achieve similar functions.

This application is based on Japanese Patent Application No. 2002-019165 filed on Jan. 28, 2002, the contents of which are hereby incorporated by reference.

What is claimed is:

1. A guide wire comprising:
a wire body;
a first coil having a helical shape, and being disposed on a distal end side of said wire body;
a second coil having a helical shape, and being disposed on a distal end side of said first coil; and
an elongate member having a section that extends in a longitudinal direction of said wire body, and made of a reshapeable material, said material being the same as a material of one of said first coil and said second coil,
wherein at least a portion of said section is located inside said second coil, and said elongate member and said one of said first coil or said second coil are a single unitary part,
wherein a distal end of said wire body is inserted into an inside of said first and second coils substantially at an internal center thereof, and
wherein a distal end of said elongate member is fixed on said second coil.

2. A guide wire comprising:
a wire body;
a first coil having a helical shape, and being disposed on a distal end side of said wire body;
a second coil having a helical shape, and being disposed on a distal end side of said first coil; and
an elongate member having a section that extends in a longitudinal direction of said wire body, and made of a reshapeable material, said material being the same as a material of one of said first coil and said second coil,
wherein at least a portion of said section is located inside said second coil, and said elongate member and said one of said first coil or said second coil are a single unitary part, and
wherein a portion of said elongate member in a longitudinal direction branches off.

3. A guide wire comprising:
a wire body;
a first coil having a helical shape, and being disposed on a distal end side of said wire body;
a second coil having a helical shape, and being disposed on a distal end side of said first coil; and
a plurality of elongate members each having a section that extends in a longitudinal direction of said wire body, and made of a reshapeable material, said material being the same as a material of one of said first coil and said second coil,
wherein at least a portion of said section is located inside said second coil, and said plurality of elongate members and said one of said first coil or said second coil are a single unitary part.

4. A guide wire comprising:
a wire body;
a helical coil having a distal end and a proximal end and being disposed on a distal end side of said wire body; and
an elongate member that extends from the proximal end of said coil, is disposed inside said coil, and is made of a material that can be reshaped, said material being the same as a material of the coil, said elongate member and said coil being a single unitary part,
in which a distal end of said elongate member is fixed internally at a central portion of said coil.

5. A guide wire comprising:
a wire body;
a first coil having a helical shape, and being disposed on a distal end side of said wire body;
a second coil having a helical shape, and being disposed on a distal end side of said first coil;
a plurality of elongate members, each of said elongate members having a section that extends in a longitudinal direction of said wire body,
wherein at least a portion of said section is located inside said second coil, and each of said elongate members is a single unitary part with said first coil or said second coil.

6. A guide wire comprising:
a body section located on a proximal side, said body section made of a material;
a section located on a distal end side away from said body section, said section made of a material of a smaller rigidity than a rigidity of said material of said body section;
a helical coil having a distal end and a proximal end, being disposed on said body section, and being radiopaque at least at the distal end thereof; and
an elongate member that can be reshaped, is made of the same material as said coil, and extends into an inside of said coil from either the distal end or the proximal end of said coil, said elongate member and said coil being a single unitary part,
in which a distal end of said section located on the distal end side away from said body section is inserted into the inside of said coil substantially at an internal center thereof.

7. A guide wire as claimed in claim 6, in which said elongate member extends from the distal end of said coil toward a proximal side and has a proximal end which is fixed to a portion of said section located on the distal end side away from said body section.

8. A guide wire comprising:
a wire body;
a first coil having a helical shape, and being disposed on a distal end side of said wire body;
a second coil having a helical shape, and being disposed on a distal end side of said first coil; and an elongate member having a section that extends in a longitudinal direction of said wire body, and made of a reshapeable material, said material being the same as a material of one of said first coil and said second coil, wherein at least a portion of said section is located inside said second coil, and said elongate member and said one of said first coil or said second coil are a single unitary part, and wherein said elongate member is formed on a distal end of said first coil and extends into an inside of said second coil.

9. A guide wire as claimed in claim 8, in which a distal end of said wire body is inserted into an inside of said first coil substantially at an internal center thereof.

10. A guide wire as claimed in claim 8, in which a distal end of said wire body is inserted into an inside of said first and second coils substantially at an internal center thereof.

11. A guide wire as claimed in claim 8, in which a distal end of said elongate member is fixed on said second coil.

12. A guide wire as claimed in claim 8, in which a distal end of said elongate member is fixed to said wire body.

13. A guide wire comprising:

a wire body;

a first coil having a helical shape, and being disposed on a distal end side of said wire body;

a second coil having a helical shape, and being disposed on a distal end side of said first coil; and an elongate member having a section that extends in a longitudinal direction of said wire body, and made of a reshapeable material, said material being the same as a material of one of said first coil and said second coil, wherein at least a portion of said section is located inside said second coil, and said elongate member and said one of said first coil or said second coil are a single unitary part, and wherein said first coil and said second coil are partially overlapping with each other and helical windings of said first coil and said second coil are joined by being intermeshed together in said overlapping area in such a way that each winding appears between the windings of the other coil.

14. A guide wire as claimed in claim 13, in which a distal end of said wire body is inserted into an inside of said first and second coils substantially at an internal center thereof.

15. A guide wire as claimed in claim 13, in which said elongate member is formed on a distal end of said first coil and extends into an inside of said second coil.

16. A guide wire as claimed in claim 13, in which said first coil and said second coil are joined together at a joined part which is fixed to said wire body.

17. A guide wire comprising:

a wire body;

a first coil having a helical shape, and being disposed on a distal end side of said wire body;

a second coil having a helical shape, and being disposed on a distal end side of said first coil; and an elongate member having a section that extends in a longitudinal direction of said wire body, and made of a reshapeable material, said material being the same as a material of one of said first coil and said second coil, wherein at least a portion of said section is located inside said second coil, and said elongate member and said one of said first coil or said second coil are a single unitary part, and wherein a transverse cross-sectional area of at least a portion of said elongate member is smaller than a transverse cross-sectional area of a wire material forming said first coil or said second coil.

18. A guide wire as claimed in claim 17, in which a distal end of said wire body is inserted into an inside of said first and second coils substantially at an internal center thereof.

19. A guide wire as claimed in claim 17, in which said elongate member is formed on a distal end of said first coil and extends into an inside of said second coil.

20. A guide wire as claimed in claim 17, in which at least a portion of said elongate member is shaped like either a flat plate or rectangular rod.

21. A guide wire as claimed in claim 17, in which said elongate member transverse cross-sectional area decreases when moving from a proximal to a distal end of the elongate member.

* * * * *